United States Patent [19]

Wada et al.

[11] Patent Number: 5,707,640
[45] Date of Patent: Jan. 13, 1998

[54] POISONOUS BAITS FOR CONTROLLING SOIL-INHABITING PESTS

[75] Inventors: Yuzuru Wada, Hachioji; Shin-ichi Tsuboi; Yuichi Otsu, both of Tochigi; Kunihiro Isono, Shimotsuga-gun; Shinzaburo Sone, Ibaraki; Takamasa Maki, Oyama; Katsuhiko Hanaki; Takahisa Abe, both of Oyama, all of Japan

[73] Assignee: Nihon Bayer Agrochem K.K., Tokyo, Japan

[21] Appl. No.: 764,769

[22] Filed: Dec. 12, 1996

Related U.S. Application Data

[63] Continuation of Ser. No. 304,967, Sep. 13, 1994, abandoned.

[30] Foreign Application Priority Data

Sep. 20, 1993 [JP] Japan ................................. 5-255309

[51] Int. Cl.⁶ .................................................. A01N 25/08
[52] U.S. Cl. ........................... 424/410; 424/418; 424/84; 514/241; 514/336; 514/357
[58] Field of Search ................................... 424/405, 407, 424/409, 410, 418, 84, 93.5, 114, 115, 195; 514/241, 336, 357

[56] References Cited

U.S. PATENT DOCUMENTS

| | | |
|---|---|---|
| 4,834,977 | 5/1989 | Kohama et al. ............... 424/405 |
| 4,985,413 | 1/1991 | Kohama et al. ............... 514/79 |
| 5,207,389 | 5/1993 | Hall et al. ..................... 241/3 |

FOREIGN PATENT DOCUMENTS

| | | |
|---|---|---|
| 190844 | 2/1985 | European Pat. Off. . |
| 0192060 | 8/1986 | European Pat. Off. . |
| 268177 | 11/1986 | European Pat. Off. . |
| 431362 | 12/1991 | European Pat. Off. . |
| 511541 | 4/1992 | European Pat. Off. . |
| 4111389 | 10/1992 | Germany . |
| 57062201 | 9/1980 | Japan . |
| 2019505 | 7/1985 | Japan . |
| 3218604 | 3/1987 | Japan . |
| 3218605 | 3/1987 | Japan . |
| 1143806 | 11/1987 | Japan . |
| 2124802 | 11/1988 | Japan . |

OTHER PUBLICATIONS

Derwent Abstracts, Abstract of JP 04-152,827 (1992).
Derwent Abstracts, Abstract of JP 04-46,101 (1992).
Derwent Abstracts, Abstract of JP 02-124,802 (1990).
Derwent Abstracts, JP 04 046, 101 (1992).

*Primary Examiner*—Neil S. Levy
*Attorney, Agent, or Firm*—Sprung Kramer Schaefer & Briscoe

[57] ABSTRACT

A poisonous bait for controlling soil-inhabiting pests comprising an active compound for controlling a soil-inhabiting pest and, as excipient, an artificial culture medium for mushrooms or the medium obtained after culture of mushrooms.

1 Claim, No Drawings

POISONOUS BAITS FOR CONTROLLING SOIL-INHABITING PESTS

This application is a continuation of application Ser. No. 08/304,967, filed on Sep. 13, 1994 which is abandoned.

The present invention relates to poisonous baits effectively used for controlling pests inhabiting soil.

Japanese Patent Application Publication No. Sho 63-26721, Japanese Patent Application Disclosures Nos. Sho 61-183201, Sho 62-19505, Sho 63-218604, Sho 63-218605, and Hei 1-143806, etc., disclose poisonous baits having improved edibility by pests.

Further, Japanese Patent Application Disclosure No. Sho 63-135308 discloses the utilization of microorganism as a pesticidal agent.

Moreover, Japanese Patent Application Disclosure No. Hei 2-124802 discloses stabilized control agents for soil-inhabiting pests comprising vegetable organic matter.

It has now been found that poisonous baits comprising active compounds for controlling soil-inhabiting pests and, as excipient, an artificial culture medium for mushrooms or the medium obtained after the culture thereof exhibit excellent pesticidal activity on soil-inhabiting pests.

The poisonous baits according to the present invention can be prepared according to conventional processes such as tabletting, briquetting, etc., wherein an artificial culture medium for mushrooms or the medium obtained after the culture thereof, is dried, followed by adding thereto the below-mentioned active compounds for controlling soil-inhabiting pests, if necessary, together with adjuvants such as binder, and the like.

Active compounds for controlling soil-inhabiting pests to be employed in the poisonous baits for controlling soil-inhabiting pests according to the present invention include organic phosphorus compounds, carbamate compounds, pyrethroid compounds, nitromethane compounds, nitroguanidine compounds, etc., and preferably:

a compound of the formula

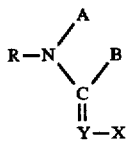

(I)

wherein
R is hydrogen, acyl, alkyl, or optionally substituted heteroarylalkyl,
A is hydrogen, alkyl or a divalent group connected to B,
B is alkyl, —S—R,

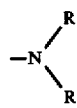

or a divalent group connected to A,
Y is =N— or

$T^1$ is hydrogen or optionally substituted alkyl, and
X is an electron attractive group.

In the active compounds for controlling soil-inhabiting pests of the general formula (I), preferably R is hydrogen, formyl, $C_{1-4}$ alkylcarbonyl, benzoyl, $C_{1-4}$ alkylsulfonyl, $C_{1-6}$ alkyl, or optionally substituted heteroarylmethyl having up to a six membered ring, at least one nitrogen ring atom and optionally one or more other hetero atoms, A is hydrogen, $C_{1-4}$ alkyl, ethylene, trimethylene, or

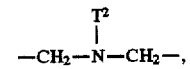

$T^2$ is hydrogen, $C_{1-4}$ alkyl or $C_{1-4}$ alkylcarbonyl,
B is $C_{1-4}$ alkyl, —S—R,

—S—, methylene or

Y is =N— or =CH—, and
X is nitro or cyano.

More preferably, R is hydrogen, formyl, acetyl, $C_{1-4}$ alkyl, 2-chloro-5-pyridylmethyl or 2-chloro-5-thiazolyl, A is hydrogen, $C_{1-4}$ alkyl, ethylene, trimethylene, or

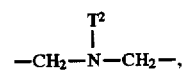

$T^2$ is methyl or ethyl,
B is $C_{1-4}$ alkyl, —S—R,

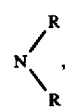

—S—, methylene or

Y is =N— or =CH—, and
X is nitro or cyano.

Still more preferably, R is 2-chloro-5-pyridylmethyl or 2-chloro-5-thiazolyl,

A is hydrogen, $C_{1-4}$ alkyl, ethylene, trimethylene, or

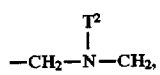

$T^2$ is methyl or ethyl,

B is $C_{1-4}$ alkyl, —S—R,

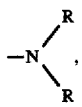

—S—, methylene or

Y is =N— or =CH—, and
X is nitro or cyano.

As concrete examples of the preferred nitro and cyano insecticidal compounds there may be mentioned N-cyano-N-(2-chloro-5-pyridylmethyl)-N'-methylacetoamidine,
1[N-(6-chloro-3-pyridylmethyl)-N-ethylamino]-1-methylamino-2-nitroethylene,
1-(2-chloro-5-pyridylmethyl)-5-methyl-2-nitroimino-hexahydro-1,3,5-triazine,
1-(2-chloro-5-thiazolylmethyl)-3,5-dimethyl-2-nitroimino-hexahyd 1,3,5-triazine,
1-(2-chloro-5-pyridylmethyl)-3,5-dimethyl-2-nitroimino-hexahydro 1,3,5-triazine,
1-(2-chloro-5-pyridylmethyl)-2-nitromethylene-imidazolidine,
1-[N-(2-chloro-5-thiazolylmethyl)-N-ethylamino]-1-methylamino-2-nitroethylene,
3-(2-chloro-5-pyridylmethyl)-2-nitromethylene-thiazolidine,
1-(2-chloro-5-pyridylmethyl)-2-(1-nitro-2-allylthioethylidene)-imidazolidine,
1-(2-chloro-5-pyridylmethyl)-2-(1-nitro-2-ethylthioethylidene)-imidazolidine,
1-(2-chloro-5-pyridylmethyl)-2-(1-nitro-2-β-methylallylthio-ethylidene)-imidazolidine,
methyl-[3-(2-chloro-5-pyridylmethyl)-1-methyl-2-nitro] guanidino-formate,
1-(2-chloro-5-pyridylmethylamino)-1-methylthio-2-nitroethylene,
1-(2-chloro-5-pyridylmethylamino)-1-methylamino-2-nitroethylene,
1-(2-chloro-5-pyridylmethyl)-3-nitro-2-methylisothiourea,
1-(2-chloro-5-pyridylmethyl)-1-methyl-2-nitroguanidine,
1-(2-chloro-5-pyridylmethylamino)-1-dimethylamino-2-nitroethylene
1-[N-(2-chloro-5-pyridylmethyl)-N-methylamino]-1-methylamino-2-nitroethylene,
1-[N-(2-chloro-5-pyridylmethyl)-N-methylamino]-1-dimethylamino-2-nitroethylene,
3-(2-chloro-5-pyridylmethyl)-1,1-dimethyl-2-nitroguanidine,
1-(2-chloro-5-pyridylmethylamino)-1-ethylamino-2-nitroethylene,
1-amino-1-[N-(2-chloro-5-pyridylmethyl)-N-methylamino]-2-nitroethylene,
3-(2-chloro-5-pyridylmethyl)-1,3-dimethyl-2-nitroguanidine,
3-(2-chloro-5-pyridylmethyl)-1,1,3-trimethyl-2-nitroguanidine,
1-amino-1-[N-(2-chloro-5-pyridylmethyl)-N-ethylamino]-2-nitroethylene,
1-[N-(2-chloro-5-pyridylmethyl)-N-n-propylamino]-1-methylamino-2-nitroethylene,
1-[N-(2-chloro-5-pyridylmethyl)-N-ethylamino]-1-ethylamino-2-nitroethylene,
3-(2-chloro-5-pyridylmethyl)-3-ethyl-1-methyl-2-nitroguanidine,
3-(2-chloro-5-thiazolylmethyl)-1-methyl-2-nitroguanidine, and
1-(6-chloro-3-pyridylmethyl)-N-nitroimidazolidin-2-ylideneamine.

To the poisonous baits for controlling soil-inhabiting pests according to the present invention there may be added insect-parasitic fungi such as Metarhizium, Metarhizium anisopliae, Beauver, and Beauveria bassiana, etc.

Excipients to be employed in the poisonous baits for controlling soil-inhabiting pests according to the present invention may be any materials used as artificial culture media for mushrooms, e.g. wood chips of broadleaved trees such as beech, oak, and the like.

As binders to be employed in the poisonous baits for controlling soil-inhabiting pests according to the present invention there may be mentioned, for example, the following substances which, however, should not be considered to limit the scope of the binders usable in the present invention:

Starch, soluble starch α-starch, dextrin, amylose, amiropectin, lignin, sodium lignin sulfonate, potassium ligninsulfonate, calcium ligninsulfonate, cellulose, methyl cellulose, ethyl cellulose, carboxymethyl cellulose, hydroxyethyl cellulose, hydroxypropyl cellulose, hydroxypropylmethyl cellulose, carboxymethyl starch, hydroxypropyl starch, sodium carboxymethyl cellulose, gum arabic, gelatin, casein, xanthane gum, alginic acid, sodium alginate, sodium silicate, polyvinyl alcohol, polypropylene glycol, polyethyelene-proplypropylene block polymer, sodium polyacrylate, and the like.

The poisonous baits according to the present invention exhibit excellent control on soil-inhabiting pests and effectively control the following soil-inhabiting pests, though they may also be used against pests other than those mentioned. Further, they can be used against all pests that emerge on and/or inhabit the soiled surface, or its vicinity.

As examples there may be mentioned the following pest and insects:

From the order of Coleoptera, *Anomala albopiosa, Anomala cuprea, Popillia japonica, Adoretus tenuimaculatus, Anomala diversa, Anomala rufocuprea, Anomala schoenfeldti, Lachnosterna morosa, Agriotes ogurae, Melanotus okinawenisis, Melanotus sakisimensis, Diabrotica spp., Aracerus fasciculatus, Sphenophorus venatus vestinus, Sceptieus griseus, Scepticus uniformis,* etc.

From the order of Diptera, *Ophiomyia lappivora, Bradisia agrestis, Delia antiqua, Delia floralis, Hylemya Platura, Dicranoptycha spp.,* etc.

From the order of Lepidoptera, *Agrotis segetum, Agrotis ipsilon,* etc.

The artificial culture medium for mushrooms and the medium obtained after the culture thereof, which are used as excipients for the poisonous baits according to the present invention have attracting action for soil-inhabiting insects, particularly larvae of gold beetles, and desirably are eaten by them.

Further, after the application of the poisonous baits according to the present invention, the portion of the excipient that has not been eaten by soil-inhabiting pests will automatically decompose in the soil to form organic manure by itself so that it will not present any environmental problem.

The poisonous baits for controlling soil-inhabiting pests according to the present invention may be used in the form of granules, tablets, rods, and the like, and can be formed according to conventional methods for the production of pesticidal formulations.

In poisonous baits for controlling soil-inhabiting pests according to the present invention, the mixing ratio by weight of the respective components may be varied over a relatively wide range and, the medium obtained after artificial culture of mushrooms may be present in from 100 to 50,000, preferably from 1,000 to 20,000 parts, by weight per part by weight of the active compound of the poisonous baits for controlling soil-inhabiting pests according to the present invention.

The dosage may be varied dependent on the farm products as well as emergency condition of soil-inhabiting pests, but it may usually be in the range of from about 0.05 to 3 kg/ha, preferably from about 0.1 to 1 kg/ha, in terms of the pesticidally active component.

The present invention provides poisonous baits for controlling soil-inhabiting pests which exhibit a number of excellent effects such as requiring no pre-treatment such as soil mixing, thus ensuring labor-saving application, keeping the dosages at a lower level, and prolonging the insecticidal activity. Moreover, the excipients employed in the instant poisonous baits decompose in the soil to form organic manure, which is an additional desirable effect.

The excellent effects exhibited by the poisonous baits for controlling soil-inhabiting pests according to the present invention are demonstrated in the following examples which, however, should not be considered to limit the scope of the present invention.

FORMULATION 1

An artificial medium used for culture of Maitake mushrooms was dried by a fluidized layer dryer. 69.97 parts of the thus obtained dried medium, 0.03 parts of an active compound for controlling soil-inhabiting pests , and 30 parts of α-starch, were mixed in a universal mixer. 30 g of the resulting mixture was tableted with the use of a mold having a diameter of 50 mm at a mold pressure of 1,000 kg/cm$^2$ to form tablets.

FORMULATION 2

An artificial medium used for culture of Maitake mushrooms was dried by a fluidized layer dryer. 69.94 parts of the thus obtained dried medium, 0.06 parts of an active compound for controlling soil-inhabiting pests, and 30 parts of crystallized cellulose, were mixed in a universal mixer. 30 g of the resulting mixture was tableted with the use of a mold having a diameter of 50 mm at a mold pressure of 1,000 kg/cm$^2$ to form tablets.

FORMULATION 3

An artificial medium used for culture of Maitake mushrooms was dried by a fluidized layer dryer. 69.96 parts of the thus obtained dried medium, 0.03 parts of an active compound for controlling soil-inhabiting pests, 0.01 parts of spores of *Metarhizium anisopliae*, and 30 parts of dextrin, were mixed in a universal mixer. 30 g of the resulting mixture was tableted with the use of a mold having a diameter of 50 mm at a mold pressure of 1,000 kg/cm$^2$ to form tablets.

BIOTEST EXAMPLE 1

Insecticidal test on *Anomala cuprea*

Test Method:

Soil of upland fields was filled into each of containers made from polypropylene (62 cm×40 cm×20 cm) and then the tablets of Formulation 1 were embedded in the soil at a depth of 5 cm in each container and lightly covered with a soil layer. Into the soil of each container were inoculated twenty heads of *Anomala cuprea* at the first instar and a carrot was placed as bait on the soil surface.

Thirty days after the inoculation of the larvae, the surviving number of the larvae was determined in each container to calculate the mortality of the insects.

This test was carried out in duplicate and the thus obtained results are shown in Table 1.

TABLE 1

| Active compounds for controlling soil-inhabiting pests under test | Dosages | | Insect mortality |
|---|---|---|---|
| | kg a.i./ha | piece/m$^2$ | (%) |
| A | 0.3 | 4 | 100 |
| A | 0.3 | 9 | 100 |
| A | 0.6 | 4 | 100 |
| A | 0.6 | 9 | 100 |
| B | 0.6 | 4 | 95 |
| B | 0.6 | 9 | 97 |
| Untreated zone | — | — | 0 |

A: 1-(6-chloro-3-pyridylmethyl)-N-nitroimidazolidin-2-ylideneamine
B: N-cyano-N-(2-chloro-5-pyridylmethyl)-N'-methylaceto amidine

BIOTEST EXAMPLE 2

Insecticidal test on *Anomala cuprea*

Test Method:

Peanut plants were cultivated in conventional manner on Kuroboku soil in an upland field consisting of a plurality of sections each having an area of 40 m$^2$ (5 m×8 m). After the plants flowered and grew, a predetermined amount of tablets of Formulation 2 were embedded in the soil of each section at a depth of 5 cm and lightly covered with a soil layer. At harvest time undamaged and damaged nutlets were surveyed for forty plants grown at the center area of each of the sections and the resulting protective values were calculated according to the following equation:

$$\text{Damage degree} = \frac{\left(\begin{array}{c}0 \times \text{number of} \\ \text{undameged} \\ \text{legumes of} \\ \text{the plants}\end{array}\right) + \left(\begin{array}{c}1 \times \text{number of} \\ \text{legumes of the} \\ \text{plants (damage} \\ \text{rate I)}\end{array}\right) + \left(\begin{array}{c}4 \times \text{number of} \\ \text{legumes of the} \\ \text{plants (damage} \\ \text{rate II)}\end{array}\right)}{(4 \times \text{the total number of legumes of the plants})} \times 100$$

Damage rate I=legumes with only devoured surface
Damage rate II=devoured nutlets observed
The results are shown in Table 2.

TABLE 2

| Active compound under test | Dosages | | Protective value |
|---|---|---|---|
| | kg a.i./ha | piece/m$^2$ | (%) |
| A | 0.3 | 9 | 90 |
| A | 0.6 | 9 | 90 |
| Untreated zone | — | — | 0 |

A: 1-(6-chloro-3-pyridylmethyl)-N-nitroimidazolidin-2-ylideneamine

It is understood that the specification and examples are illustrative but not limitative of the present invention and that other embodiments within the spirit and scope of the invention will suggest themselves to those skilled in the art.

What is claimed is:

1. A poisonous bait for controlling a pest within the order of Coleoptera, Deptera and Lepidoptera, which comprises a pesticide active against said pest selected from the group consisting of:

N-cyano-N-(2-chloro-5-pyridylmethyl)-N'-methylacetoamidine,

1-[N-6-chloro-3-pyridylmethyl-N-ethylamino]-1-methylamino-2-nitroethylene,

1-[2-chloro-5-thiazolylmethyl-3,5,-dimethyl-2-nitroaminohexahydro-1,3,5-triazine and 1-(6-chloro-3-pyridylmethyl)-N-nitroimidazolidin-2-ylideneamine, and wood chips of a beech or oak tree as both excipient and attractant, said wood chips having first been used as a culture medium for mushrooms.

* * * * *